United States Patent [19]

Osborn, III et al.

[11] Patent Number: 5,007,906
[45] Date of Patent: Apr. 16, 1991

[54] DECOUPLED SANITARY NAPKIN

[75] Inventors: Thomas W. Osborn, III, Cincinnati; Deborah C. Schmitz, West Chester, both of Ohio

[73] Assignee: The Procter & Gamble Company, Cincinnati, Ohio

[21] Appl. No.: 429,252

[22] Filed: Oct. 27, 1989

[51] Int. Cl.$^5$ .................. A61F 13/15; A61F 13/20
[52] U.S. Cl. .................. 604/385.1; 604/386; 604/399; 604/387
[58] Field of Search .............. 604/385.1, 397, 398, 604/399, 400, 386, 387

[56] References Cited

U.S. PATENT DOCUMENTS

| 1,959,282 | 5/1934 | Bade | 604/399 |
|---|---|---|---|
| 3,084,692 | 4/1963 | Atkinson | 128/290 |
| 3,604,423 | 9/1971 | Fraser | 604/385.1 |
| 3,814,100 | 6/1974 | Nystrand et al. | 128/287 |
| 3,865,112 | 2/1975 | Roeder | 128/290 |
| 3,926,189 | 12/1975 | Taylor | 128/287 |
| 3,954,107 | 5/1976 | Chesky et al. | 128/290 |
| 4,029,101 | 6/1977 | Chesky et al. | 128/290 |
| 4,338,939 | 7/1982 | Daville | 604/399 |
| 4,425,130 | 1/1984 | DesMarais | 604/389 |
| 4,505,706 | 3/1985 | Erpicum et al. | 604/389 |
| 4,605,405 | 8/1986 | Lassen | 604/389 |
| 4,609,373 | 9/1986 | Johnson | 604/385.1 |
| 4,787,896 | 11/1988 | Houghton et al. | 604/385.1 |
| 4,790,839 | 12/1988 | Ahr | 604/367 |

Primary Examiner—Randall L. Green
Assistant Examiner—Paul Prebilic
Attorney, Agent, or Firm—Larry L. Huston; John M. Pollaro; Frederick H. Braun

[57] ABSTRACT

A sanitary napkin having a top sheet and an absorbent core associated with the topsheet is disclosed. The topsheet and associated core are decoupled from the backsheet of the sanitary napkin so that the topsheet and backsheet may be separated in the Z-direction. The sanitary napkin has a joined transverse edge connecting the top sheet and backsheet and forming a hinge to facilitate the Z-direction separation. The sanitary napkin further controls the amount of separation of the topsheet and associated core from the backsheet. A preferred way to control the amount of separation of the topsheet and associated core from the backsheet is longitudinally oriented pleats.

9 Claims, 1 Drawing Sheet

DECOUPLED SANITARY NAPKIN

FIELD OF THE INVENTION

The invention disclosed herein relates to disposable absorbent articles, particularly sanitary napkins, and more particularly sanitary napkins having a means for providing improved body contact.

BACKGROUND OF THE INVENTION

Sanitary napkins and related disposable absorbent articles which provide for the collection of menses and other bodily discharges are well known in the art. It has long been an object of sanitary napkins to readily intercept menses upon discharge from the wearer. Such sanitary napkins have long had a means, typically pressure sensitive adhesive, for affixing the sanitary napkin to the undergarment of the wearer and maintaining the sanitary napkin in the proper position to intercept the discharged menses.

However, the undergarment may not, in fact, move in concert with the body of the wearer. Specifically, the crotch of the undergarment of the wearer may not remain in constant registration with and position relative to the vaginal opening. Also, as the wearer spreads her legs, walks, sits, etc., the sanitary napkin may not flex and twist with the undergarment—stressing the means for affixing the sanitary napkin to the undergarment of the wearer. In fact, the pressure sensitive adhesive may become detached from the undergarment, further allowing the sanitary napkin to shift from the desired position and registration.

Several attempts in the art have been made to provide a sanitary napkin which may be attached to the undergarment of the wearer and also maintain the constant position with respect to the body of the wearer. For example, U.S. Pat. No. 4,425,130 issued Jan. 10, 1984 to DesMarais discloses a sanitary napkin having decoupled components joined at the transverse edges.

Other attempts have been made in the art to provide a sanitary napkin which maintains contact of the topsheet with the body of the wearer. For example, U.S. Pat. No. 4,804,380, issued Feb. 14, 1989 to Lassen et al. discloses a three dimensionally shaped sanitary protecting device which claims to readily fit and align itself with the wearer's anatomy. However, this teaching does not allow for the aforementioned independence of movement between the body of the wearer and the undergarment of the wearer.

Other attempts in the prior art to provide improved body contact are illustrated by U.S. Pat. No. 2,747,575 issued May 29, 1956 to Mercer. This patent discloses a catamenial bandage having a longitudinal hump which bulges towards and may contact the body of the wearer. However, this teaching suffers from the drawback that the bandage requires transverse compressive forces to cause the topsheet to bulge towards the labia and no means for controlling the type or degree of bulging is provided.

None of the sanitary napkins according to the prior art provide separation and independent movement of the topsheet and backsheet and a means for controlling such separation and independent movement. Also the sanitary napkins of the prior art do not provide a means for maintaining labia contact without transversely compressive forces being applied to the sanitary napkin.

It is an object of this invention to provide a sanitary napkin which more readily intercepts menses as it is discharged. Also, it is an object of this invention to provide a sanitary napkin which maintains better contact with the wearer throughout the range of normal movements encountered while the sanitary napkin is worn. Finally, it is an object of this invention to provide sanitary napkin which provides controlled and independent movement of the components relative to both the undergarment of the wearer and to the vaginal opening of the wearer.

SUMMARY OF THE INVENTION

The present invention comprises a sanitary napkin having two spaced apart longitudinally oriented edges and two spaced apart transversely oriented edges. The sanitary napkin has a liquid pervious topsheet, a liquid impervious backsheet joined to the topsheet along one transverse edge and unattached to the topsheet along the other transverse edge, so that the topsheet may be separated from the backsheet. The sanitary napkin further has an absorbent core between the topsheet and the backsheet and associated with the topsheet. The sanitary napkin is provided with a means for controlling the separation of the topsheet from the backsheet.

The means for controlling the separation of the topsheet from the backsheet comprises a longitudinal pleat which constrains the separation of the topsheet from the backsheet. In one embodiment the joined transverse edge is generally coincident with the transverse edge located at the perimeter of the sanitary napkin. In another embodiment, the joined transverse edge is longitudinally inboard of the perimeter and the sanitary napkin has unattached transverse edges in front of and behind the joined transverse edge.

BRIEF DESCRIPTION OF THE DRAWINGS

While the Specification concludes with claims particularly pointing out and distinctly claiming the presenting invention, it is believed the same will be better understood from the following description taken in conjunction with the accompanying drawings wherein like parts are given the same reference numeral, similar or analogous parts are designated with a prime symbol, and:

DETAILED DESCRIPTION OF THE INVENTION

Figure 1:
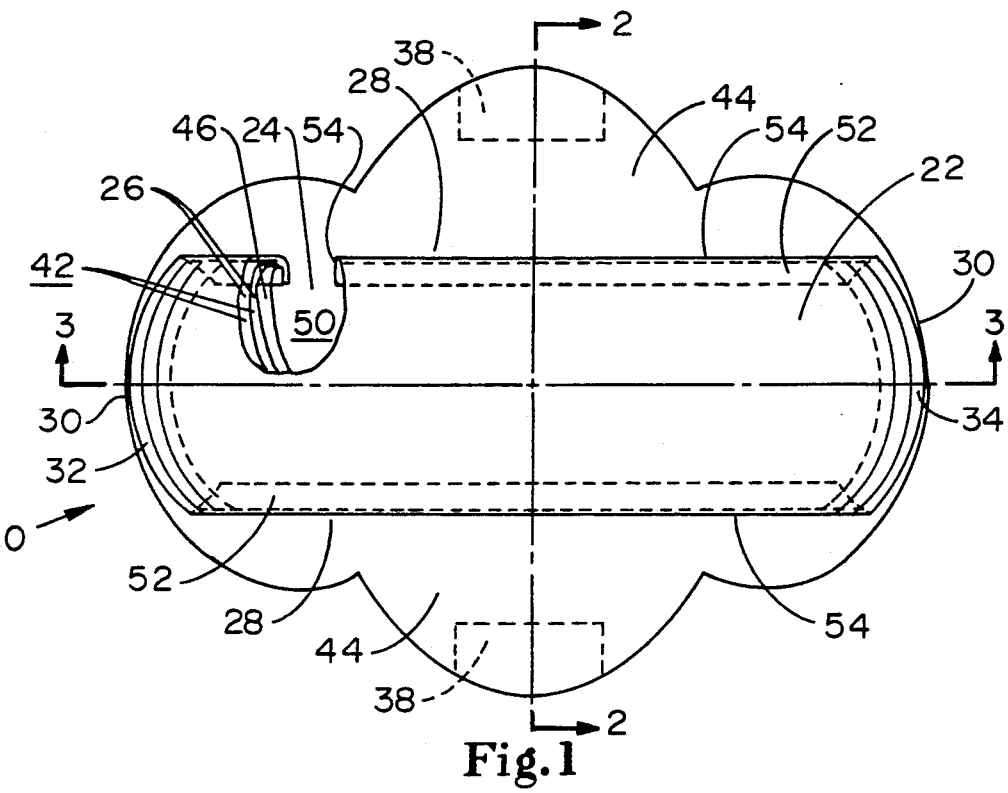
FIG. 1 is a top plan view, partially shown in cutaway, of a sanitary napkin according to the present invention.

As illustrated in FIG. 1 a decoupled sanitary napkin 20 according to the present invention has a liquid pervious topsheet 22 which is oriented towards and contacts the body of the wearer, a liquid impervious backsheet 24 which is oriented towards and contacts the undergarment of the wearer and an absorbent core 26 intermediate the topsheet 22 and backsheet 24. The core 26 is associated with the topsheet 22. The topsheet 22 is decoupled from the backsheet 24. As used herein the term "decoupled" refers to the independence of movement of two components of the sanitary napkin 20 and requires separability of such components.

The sanitary napkin 20 is defined by two longitudinal ends 28 and two transverse ends 30. As used herein the term "longitudinal" refers to a line, axis or direction generally aligned with the vertical plane which bisects the standing wearer into left and right body halves. The term "transverse" refers to the line, axis or direction generally orthogonal the longitudinal direction and lying within the plane of the sanitary napkin 20. The sanitary napkin 20 is typically longer in the longitudinal dimension than in the transverse dimension.

Figure 2:
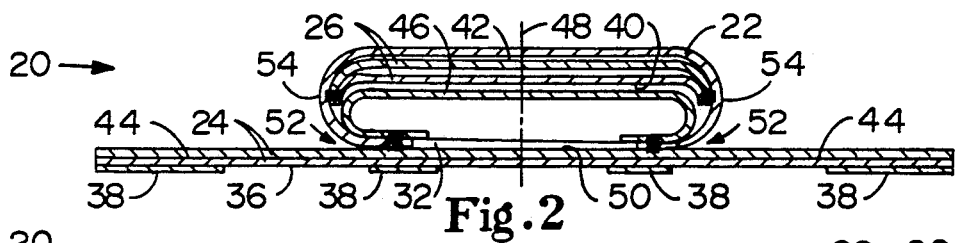
FIG. 2 is a vertical sectional view taken along lines 2—2 of FIG. 1, showing the sanitary napkin articulated to the closed position.
Figure 3:
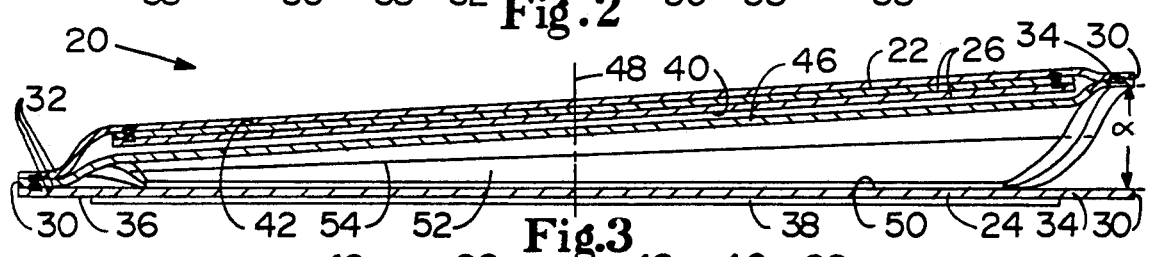
FIG. 3 is a vertical sectional view taken along lines 3—3 of FIG. 1, showing the sanitary napkin articulated to the open position.

The topsheet 22 and backsheet 24 are joined together at one transverse edge 32 and unattached to each other at the other transverse edge 34. Typically, the transverse edge 32 at which the topsheet 22 and backsheet 24 are joined is oriented towards the front of the sanitary napkin 20 and wearer while the sanitary napkin 20 is being worn and the unattached transverse edges 34 are oriented towards the rear of the wearer as the sanitary napkin 20 is being worn. As illustrated in FIGS. 1-3, the joined transverse edge 32 is generally coincident a transverse end 30.

As used herein the term "joined" refers to the condition where a first member or component is attached, or connected, to a second member or component either directly; or indirectly, where the first member or component is attached, or connected, to an intermediate member or component which in turn is attached, or connected, to the second member or component. The relationship between the first and second joined members or components is intended to remain for the life of the members or components. As used herein the term "unattached" refers to the condition where two members or components are not joined or otherwise intended to remain in contacting and adjacent relationship during the useful life of the disposable absorbent article. The term "affixed" refers to a temporary contacting relationship between two members or components of the sanitary napkin 20. As used herein, the term "associated" comprises integral, joined, affixed, indirectly and weakly linked relationships.

Examining the components in more detail, the topsheet 22 is the component of the sanitary napkin 20 which is oriented towards and contacts the body of the wearer and receives bodily discharges. The topsheet 22 is liquid pervious and should be flexible and nonirritating to the skin. As used herein the term "flexible" refers to materials which are compliant and readily conform to the shape of the body or respond by easily deforming in the presence of external forces. Preferably the topsheet 22 is not noisy, to provide discretion for the wearer. The topsheet 22 should be clean in appearance and somewhat opaque to hide the bodily discharges collected in and absorbed by the core 26.

The topsheet 22 should further exhibit good strike-through and rewet characteristics, permitting bodily discharges to rapidly penetrate the topsheet 22 to the core 26, but not flow back through the topsheet 22 to the skin of the wearer. A suitable topsheet 22 may be made from nonwoven materials and perforated polyolefinic films.

The topsheet 22 has a plurality of apertures to permit liquids deposited thereon to pass through to the core 26. Such apertures may, but need not, be present in the flaps 44. An apertured polyolefinic film topsheet 22 having about 5 to about 60 percent open area, typically about 25 percent open area, and a thickness of about 0.01 to about 0.05 millimeters is suitable.

If desired, the topsheet 22 may be sprayed with a surfactant to enhance fluid penetration to the core 26. The surfactant is typically nonionic and should be non-irritating to the skin. A surfactant density of about 0.01 milligrams per square centimeter of topsheet 22 area is suitable. A suitable surfactant is sold by the Glyco Chemical, Inc. of Greenwich, Conn., as Pegosperse 200 ML.

It is recognized that the topsheet 22 may have absorbent capacity, if the core 26 has a capillary system or a Z-direction system of fibers. This provides an integral topsheet 22 and associated core 26 structure. A nonwoven topsheet 22 is typically used for this purpose.

A particularly suitable topsheet 22 may be made in accordance with U.S. Pat. No. 4,342,314 issued Aug. 3, 1982 to Radel et al. and U.S. Pat. No. 4,463,045 issued July 31, 1984 to Ahr et al., which patents are incorporated herein by reference for the purpose of disclosing particularly preferred executions of liquid pervious topsheets. An elastically inextensible topsheet 22 made of model X-3265 or model P1552 apertured formed film sold by the Ethyl Corporation, Visqueen Division, of Terre Haute, Ind. has been found to work well.

The backsheet 24 may be any flexible, liquid impervious material, such as a polyolefinic film, and prevents discharges collected by and contained in the sanitary napkin 20, particularly discharges absorbed by the core 26, from escaping the sanitary napkin 20 and soiling the clothing and bedding of the wearer. Preferably the backsheet 24 is not noisy, to provide discretion for the wearer.

The backsheet 24 may also be impervious to malodorous gases generated by absorbed bodily discharges, so that the malodors do not escape and become noticed by the wearer. A low density polyethylene backsheet 24 about 0.01 to about 0.05 millimeters in thickness, preferably about 0.02 millimeters in thickness, has been found to work well. Particularly, a polyethylene film, such as is sold by the Ethyl Corporation, Visqueen Division, under model XP-39385 has been found particularly well suited for this purpose.

In a particularly preferred embodiment, the backsheet 24 is slightly larger than the topsheet 22 and intermediate absorbent core 26. In such an embodiment, the topsheet 22 and intermediate absorbent core 26 are peripherally circumscribed by the backsheet 24 which has a radial margin of about 0.5 centimeters to about 1.5 centimeters, preferably about 1.0 centimeter, from the edge of the topsheet 22. This geometry provides a marginal area of protection should the core 26 become overloaded or the sanitary napkin 20 otherwise fail. In such an embodiment the backsheet 24 and flaps 44 are preferably unitary and coextensive.

Referring to FIG. 2, if desired, the outwardly oriented face 36 of the backsheet 24 may comprise a means for attaching 38 the sanitary napkin 20 to the undergarment of the wearer. Preferred attaching means 38 include mechanical fasteners or, more preferably, pressure sensitive adhesive 38. The pressure sensitive adhesive 38 may be applied to the outwardly oriented face of the backsheet 36 in two parallel lines or two symmetrically opposite, convex outwardly oriented lines. The lines may be about 5 to about 20 millimeters in width. Alternatively, the adhesive 38 may be applied to the backsheet 24 in a generally centered rectangular patch (not shown) covering about 30 to about 70 percent of the area of the outwardly oriented face of the backsheet 36. Another alternative, as illustrated, is adhesive 38 longitudinally centered and disposed near the distal end of each flap 44. Suitable adhesive 38 is supplied as 0.6 mil pass Century Adhesive A305-4 by Anchor Continental, Inc., 3 Sigma Division, of Covington, Ohio.

Referring back to FIG. 1, the absorbent core 26 is the means for collecting and containing bodily discharges, particularly menses, deposited thereon or which otherwise traverses through the liquid permeable topsheet 22. The core 26 is the component of the sanitary napkin 20 which receives and retains the bodily discharges. The core 26 is conformable and nonirritating to the skin. The core 26 may be rectangular or hourglass shaped. The core 26 preferably has two opposed faces, one face 40 oriented towards the backsheet 24 and one face 42 oriented towards the topsheet 22.

Suitable core 26 materials include combinations of airfelt, such as cellulose wadding, and fibrated commu- nition pulp; layers of tissue paper; and absorbent gelling materials. If a tissue paper core 26 is selected, tissue paper made in accordance with U.S. Pat. No. 4,191,609 issued Mar. 4, 1980 to Trokhan and incorporated herein by reference to show a particularly preferred tissue paper is suitable for the sanitary napkin 20 described herein.

If it is desired to incorporate absorbent gelling materials into the core 26 of the sanitary napkin 20, absorbent gelling materials made in accordance with U.S. Pat. No. 4,654,039 issued Mar. 31, 1987 to Brandt et al. and incorporated herein by reference for showing particularly preferred absorbent gelling materials are suitable. A suitable laminate of absorbent gelling materials and tissue may be purchased from the Grain Processing Corporation of Muscatine, Iowa, under Model Number L535.

The core 26 need not have a total absorbent capacity much greater than the total amount of bodily discharges to be absorbed. The core 26 is preferably narrow and thin, to be comfortable to the wearer. For the embodiment described herein the capacity of the core 26 should be at least about 2 grams of 0.9 percent saline solution. Suitable saline solution is sold by Travenol Laboratories of Deerfield, Ill.

The core 26 should be sized to register with the topsheet 22 and backsheet 24. The core 26 is preferably interposed between the topsheet 22 and backsheet 24 to prevent the absorbent material of the core 26 from shredding or becoming detached while the sanitary napkin 20 is worn and to ensure proper containment of bodily discharges. This arrangement also provides for a unitary assembly.

The sanitary napkin 20 is preferably relatively flexible, so as to provide comfort for the wearer. By separating the topsheet 22 and associated core 26 from the backsheet 24, the flexibility of the portion of the sanitary napkin 20 which is adjacent and conforms to the wearer's body is enhanced and increased. This occurs because the stiffness imparted by the backsheet 24, and any associated components, will be generally less noticeable, due to subcomponents being decoupled and further from the body of the wearer. Furthermore, the enhanced flexibility allows the topsheet 22 and associated core 26 to stay closer to and in conformance with the body of the wearer.

A particularly preferred and illustrated core 26 has two layers. The layer closer to the topsheet 22 is made of a wet laid tissue having a wet tensile strength of about 15 grams per centimeter of width. The layer closer to the backsheet 24 is made of an air laid tissue containing about 0.005 grams per square centimeter absorbent gelling materials. This dual layered core 26 arrangement provides the advantage that the tissue layer prevents contact of the absorbent gelling material with the body of the wearer.

Further, the sanitary napkin 20 preferably has a caliper of less than about 10 millimeters and more preferably less than about 7 millimeters, as measured with a comparator gage having an approximately 80.0 gram test weight and an approximately 10 gram comparator foot having a diameter of about 2.54 centimeters and a contact surface area of approximately 5.1 square centimeters. Also, the sanitary napkin 20 of the present invention should have a topsheet 22 surface area of at least about 100 square centimeters to prevent discharged fluids from missing the target of the absorbent article.

If desired, the sanitary napkin 20 may further comprise flaps 44 extending outwardly from each longitudinal edge of the sanitary napkin 20. The flaps 44 may be made in accordance with the teachings of U.S. Pat. Nos. 4,589,876, issued May 20, 1986 to Van Tilburg and 4,687,478, issued Aug. 18, 1987 to Van Tilburg, which patents are incorporated herein by reference for the purpose of showing particularly preferred flaps used in conjunction with sanitary napkins 20.

As illustrated in FIG. 2, a sanitary napkin 20 according to the present invention may further comprise a liquid impervious interliner 46 which is associated with the core 26 and intermediate the core 26 and backsheet 24. The interliner 46 is the first constraint for bodily discharges which migrate towards the backsheet 24. However, if the interliner 46 is omitted, or discharges penetrate the interliner 46, such discharges will be generally intercepted and retained by the backsheet 24. The interliner 46 is generally coextensive with and preferably generally registered with the core 26. The interliner 46 may be heat sealed or, preferably, adhesively joined to the absorbent core 26 with two-sided surgical tape Number 1524 made by the Minnesota Mining and Manufacturing Company of St. Paul, Minn.

The interliner 46 may be joined to the core 26 throughout the entire surface area of the interliner 46, but this arrangement results in a sanitary napkin 20 of lower flexibility. The interliner 46 is preferably peripherally joined to the face 40 of the core 26 which is oriented towards the backsheet 24 and prevents fluids absorbed by and retained in the core 26 from leaking out of the sanitary napkin 20 and staining the clothing of the wearer. The interliner 46 more preferably wraps the longitudinal ends 28 of the core 26 and is peripherally joined to the face 42 of the core 26 which is oriented towards the topsheet 22 in the areas adjacent the longitudinal ends 28.

The interliner 46 is preferably relatively thin, having a thickness less than or equal to that of the backsheet 24, and is flexible, so that as the sanitary napkin 20 is worn and articulates between the open and closed positions, discretion is provided for the wearer. An interliner 46 having a thickness of no greater than about 0.02 millimeters is suitable. A suitable interliner 46 may be made from the low density polyethylene material, described above, used for the backsheet 24 or from X-7644 low density polyethylene film sold by the Ethyl Corporation, Visqueen Division of Terre Haute, Ind.

If the interliner 46 is liquid impervious, it is not necessary that the backsheet 24 also be liquid impervious. In such an embodiment, the interliner 46 functions as a backsheet and the backsheet 24 need only be liquid resistant. As used herein "liquid resistant" refers to the property of a material which impedes the transport of liquids through and past such material and is inclusive of liquid impervious materials.

The sanitary napkin 20 according to the present invention has the core 26 and associated topsheet 22 decoupled from the backsheet 24 and further comprises a means to control the amount of decoupling which occurs in the Z-direction. As used herein the "Z-direction" is the direction which is orthogonal the plane of the sanitary napkin 20 when it is in the flat, laid out condition of FIG. 1. The axis 48 of the Z-direction is generally oriented towards the wearer while the sanitary napkin 20 is worn. The X-Y plane is orthogonal the Z-direction axis 48, encompasses the longitudinal and transverse axes and is coincident with the plane of the inwardly oriented surface of the backsheet 50 when the sanitary napkin 20 is in the flat, laid out condition of FIG. 1.

As illustrated in FIGS. 2 and 3, the sanitary napkin 20 according to the present invention articulates between the closed and open positions. In the "closed position" of FIG. 2 the unattached transverse edges 34 of the topsheet 22 and backsheet 24 are generally proximate and preferably adjacent. In the "open position" of FIG. 3, the unattached transverse edges 34 of the topsheet 22 and backsheet 24 are separated in the Z-direction, relative to each other, from their respective closed position locations.

The means for controlling the separation of the topsheet 22 from the backsheet 24 prevents the sanitary napkin 20 from unintended gross deformation or exceeding the open position. As used herein a "means for controlling the separation of the topsheet from the backsheet" is any component which limits the relative Z-direction separation of the topsheet 22 and the backsheet 24.

The joined transverse edge 32 of the sanitary napkin 20 functions like a hinge, allowing the balance of the sanitary napkin 20 to articulate about the transverse line coincident this transverse edge. The joined transverse edge 32 typically comprises a topsheet 22 joined to the backsheet 24, and a core 26 and interliner 46 interposed between the topsheet 22 and the backsheet 24 at the joined transverse edge 32. Components which change relative positions in the Z-direction, away from each other, are said to "separate."

For a sanitary napkin 20 having a topsheet 22 longitudinal dimension of about 13 to about 35 centimeters, the unattached transverse edges 34 should have a maximum separation in the Z-direction of about 1 to about 6 centimeters, and preferably about 3 to 4 centimeters. If the maximum Z-direction separation is less, the desired decoupling of the sanitary napkin 20 components may not occur—so that contact may not be maintained with both the undergarment by the backsheet 24 and the body of the wearer by the topsheet 22. Conversely, if a greater maximum Z-direction separation occurs at the unattached transverse edges 34, the sanitary napkin 20 may appear limp and be uncomfortable to wear. Further, collapsing in the X-Y plane, particularly in the transverse direction, is more likely to occur—causing that the topsheet 22 and backsheet 24 of the sanitary napkin 20 to become mutually misaligned.

Similarly, the magnitude of the Z-direction separation of the longitudinally centered portion of the sanitary napkin 20, which portion is intended to be placed in the proximity of or registered with the vaginal opening, is important and should be considered. Frequently, the sanitary napkin 20 is isomerically distributed about and longitudinally centered on the vagina of the wearer, i.e. the vagina will be registered with the transverse axis. If so registered, the Z-direction separation at the transverse axis will be about one-half of the Z-direction separation at the unattached transverse edges 34, i.e. preferably about 0.5 to 3 centimeters, and more preferably about 1.5 to 2 centimeters.

The amount of separation of the unattached transverse edges 34 of the topsheet 22 and backsheet 24 may be measured by attaching the outwardly oriented face 36 of the backsheet 24, using the attachment means 38 provided for attaching the backsheet 24 to the undergarment of the wearer, to a rigid, flat, planar surface and maintaining the backsheet 24 in contact with and parallel to this surface. The intersection of the longitudinal centerline and unattached transverse edge 34 of the topsheet 22 is located.

This intersection is raised in the Z-direction, generally perpendicular to the flat, planar surface, until the topsheet 22 is fully articulated from the flat, planar surface and the sanitary napkin 20 is in the open position. The unattached transverse edges 34 of the core 26 and topsheet 22 travel in an arc concavely oriented towards the joined transverse edge 32 and the flat, planar surface. The topsheet 22 and core 26 may bow to a slightly concave downward configuration, as the longitudinal center of the topsheet 22 is being raised and the longitudinal edges of the topsheet 22 and core 26 are restrained by the means for controlling the separation of the topsheet 22 from the backsheet 24.

One suitable method for lifting the topsheet 22 and core 26 from the flat, planar surface is to insert a thin blade (such as a rule or scale about 2.5 centimeters wide and about 1 millimeter thick) oriented in the X-Y plane, between the core 26 and backsheet 24. The end of the blade is inserted to the joined transverse edges 32. The opposite end of this blade is lifted away from the flat, planar surface while maintaining the inserted end of the blade on the backsheet 24 and adjacent the joined transverse edges 32.

The end of the blade is lifted away from the flat, planar surface until the sanitary napkin 20 is articulated to the open position. When the open position is reached, the Z-direction distance between the face 50 of the backsheet 24 oriented towards the core 26 and the face 40 of the core 26 oriented towards the backsheet 24 is measured perpendicular to the flat, planar surface. A separate scale, oriented in the Z-direction and generally orthogonal the flat, planar surface, may be used for this measurement. The measurement is taken at the longitudinal position coincident with the unattached transverse edge 34 of the topsheet 22 while the sanitary napkin 20 is articulated to the open position.

Another measure of the desired separation of the core 26 and backsheet 24 is the included angle $\alpha$ which the face 40 of the core 26 oriented towards the backsheet 24 and the face 50 of the backsheet 24 oriented towards the core 26 define when the sanitary napkin 20 is articulated to the open position. Such a measurement is independent of the longitudinal length of the sanitary napkin 20 and, therefore, is generally preferred over measuring the length of the Z-direction separation of the core 26 and backsheet 24.

The measurement of this included angle $\alpha$ may be accomplished in a manner similar to that described above, for measuring the amount of Z-direction separation of the core 26 and backsheet 24. The sanitary napkin 20 is affixed, using the means for attaching 38 the sanitary napkin 20 to the undergarment of the wearer, to a rigid flat, planar surface. The topsheet 22 and associated core 26 are articulated to the open position as described above. The amount of Z-direction separation is measured, as described above. The distance taken along the plane of the topsheet 22 from the inboardmost juncture of the joined transverse edges 32 to the intersection of the unattached transverse edge 34 of the topsheet 22 and the longitudinal centerline is also measured.

The included angle $\alpha$ is then found by triangulating these two measurements and is equivalent to the arcsin of the distance of Z-direction separation perpendicular to the flat, planar surface divided by the topsheet 22 length taken from the inboard position of the joined transverse edge 32 to the intersection of the longitudinal centerline and unattached edge of the topsheet 22. Preferably the included angle $\alpha$ of the sanitary napkin 20 is between about 3° and about 60°, and more preferably between about 7° and about 20°.

One suitable means for controlling the amount of separation of the topsheet 22 and associated core 26 from the backsheet 24 is longitudinally oriented pleats 52 which form a connection Joining the topsheet 22 to the backsheet 24. As used herein a "longitudinally oriented pleat" is a component of the sanitary napkin 20 typically but not necessarily having a length in the longitudinal direction generally equivalent the longitudinal dimension of the shorter of the topsheet 22 and backsheet 24 and a longitudinally oriented fold line 54, so that dual, or greater, Z-direction layers of the material are provided throughout the length of the fold line 54.

It is to be recognized that a foreign lamina or material may be interposed between the dual layers of the longitudinally oriented pleat 52. The longitudinally oriented pleats 52 may be an extension of the topsheet 22, an extension of the backsheet 24, or a separate piece of material having one end joined to the topsheet 22 and one end joined to the backsheet 24. Preferably two longitudinally oriented pleats 52 are provided, one at each longitudinal end 28 of the sanitary napkin 20.

Referring back to FIG. 2, a preferred longitudinally oriented pleat 52 is made from the topsheet 22, and comprises a C-fold. The longitudinal ends 28 of the topsheet 22 which form the C-fold are folded under the portion of the topsheet 22 laterally inboard of the longitudinal ends 28 and joined to the backsheet 24. Joining may be accomplished by heat sealing or adhesive bonding. The Number 1524 surgical tape sold by the Minnesota Mining and Manufacturing Company is suitable for this purpose. The longitudinally oriented pleat 52 may have a fold line 54 between the distal end of the C-fold which is joined to the backsheet 24 and the laterally corresponding layer of material, displaced in the Z-direction, which forms part of the longitudinally oriented pleat. If a C-fold type longitudinally oriented pleat 52 is selected, the fold line 54 is generally coincident with the apex of the C-fold.

Each half of the C-fold is concave inwardly oriented towards the longitudinal centerline of the sanitary napkin 20. In this arrangement, the longitudinal ends 28 of the topsheet 22 are folded underneath the core 26 and joined to the backsheet 24. In the closed position the C-fold is collapsed, allowing the pleats of the C-fold to transversely extend and have material flaccid in the Z-direction. When the sanitary napkin 20 is articulated to the open position, the fold lines 54 of the longitudinally oriented pleat 52 are lifted, away from the backsheet 24 in the Z-direction, removing the slack from the flaccid material of the C-fold and constraining the Z-direction separation when the C-folds are fully extended. Preferably, the transverse depth of each longitudinal edge of the longitudinally oriented pleat 52 ranges from about 2 millimeters to about 15 millimeters, and is preferentially about 5 millimeters to about 8 millimeters.

Alternatively, a suitable means for controlling the separation of the topsheet 22 and backsheet 24 is an accordion style (not shown) longitudinally oriented pleat 52. Such a longitudinally oriented pleat 52 has two distal ends, one affixed to the inwardly oriented face of the topsheet 22 and one affixed to the inwardly oriented face of the backsheet 50; a central section generally centered between the distal ends and longitudinally oriented fold lines 54 defining the segments of the accordion style longitudinally oriented pleat 52. An accordion pleat provides the advantage that relatively large Z-direction separation is feasible, without requiring longitudinally oriented pleats 52 having an excessive lateral depth.

The C-fold, accordion style pleat, or other longitudinally oriented pleat 52 may be longitudinally tapered, or, preferably for ease of manufacture, of longitudinally constant geometry as shown. If longitudinally tapered, the C-fold or accordion style pleat may provide the advantage of generally uniform constraint along the entire longitudinal distance between the transverse edges of the topsheet 22 and backsheet 24 which are subtended by such longitudinally oriented pleat. If a longitudinally constant geometry C-fold or accordion style pleat is selected, the depth of the C-fold or accordion style pleat at the unattached transverse edges 34 of the topsheet 22 and backsheet 24 will control the maximum transverse and Z-direction separation, and hence decoupling, of the topsheet 22 and backsheet 24.

The longitudinally oriented pleat 52 may be significantly shorter in longitudinal dimension than the other components, such as the topsheet 22 or the backsheet 24, of the sanitary napkin 20. The longitudinally oriented pleat 52 may be of any longitudinal dimension desired, so long as such longitudinally oriented pleat 52 can resist Z-directional separation forces and prevent the sanitary napkin 20 from articulating past the intended open position. It is, however, important that the longitudinally oriented pleat 52 be longitudinally registered with the portion of the sanitary napkin 20 of which it is desired to control the Z-direction separation, typically the unattached transverse edges 34 or the lateral centerline of the sanitary napkin 20. If desired, discrete longitudinally oriented pleats 52 may be provided at both of these locations, or at other locations as desired.

Figure 4:
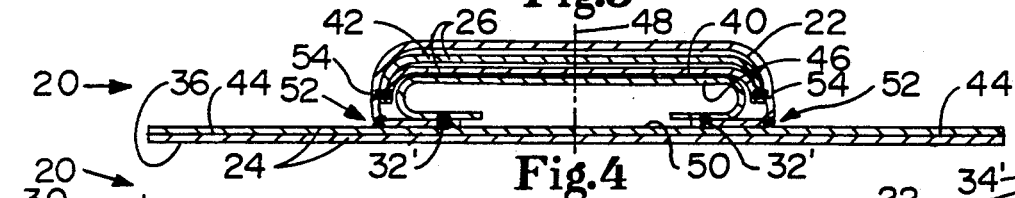
FIG. 4 is a vertical sectional view of a second embodiment, having the transverse edge of the topsheet and backsheet joined only at the longitudinal edges and about one-third of the distance from the perimeter.

As illustrated in FIG. 4, the joined transverse edge 32' where the topsheet 22 and backsheet 24 are joined need not be coincident with the perimeter of the sanitary napkin 20, particularly a transverse end 30, and may be longitudinally offset towards the lateral axis. If such an embodiment is selected, the joined transverse edge 32' should be inset from the transverse end 30 of the sanitary napkin 20 at least about one-fifth of the longitudinal dimension of the sanitary napkin 20. Preferably, the transverse edge 32' where the topsheet 22 and backsheet 24 are joined is generally not longitudinally centered, so that the topsheet 22 and core 26 may lift into the labial tissue and more readily intercept menses upon discharge. A particularly preferred location of the joined transverse edge 32' is approximately one-third of the longitudinal distance from either transverse end 30.

Figure 5:
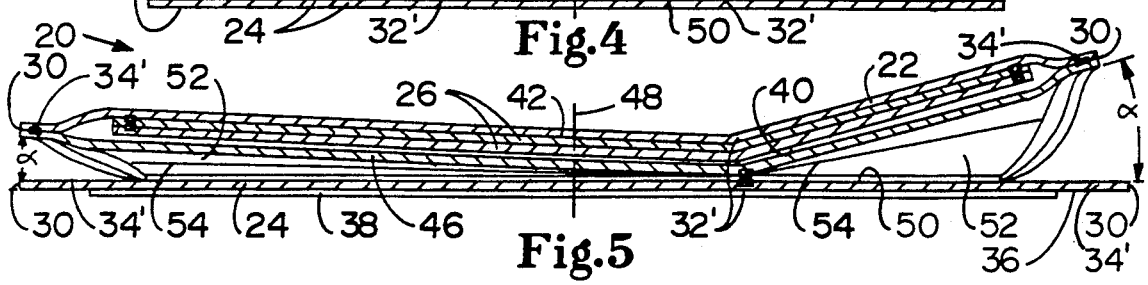
FIG. 5 is a vertical sectional view of the sanitary napkin of FIG. 4, showing the sanitary napkin articulated to the open position with both the front and rear unattached transverse edges displaying Z-direction separation.

As illustrated in FIG. 5, this arrangement provides a sanitary napkin 20 having two unattached transverse edges 34'. The two unattached transverse edges 34' can independently articulate and move in the Z-direction. Thus, the portions of the sanitary napkin 20, particularly the unattached transverse edges 34', located both in front of and behind the joined transverse edge 32' may be separated in the Z-direction. This structure provides an additional manner in which the topsheet 22 which can maintain contact with the body of the wearer.

It will be apparent to one skilled in the art that the transverse edge 32', regardless of its longitudinal position, where the topsheet 22 and backsheet 24 are joined, need not be joined across and throughout the entire width of the sanitary napkin 20. The topsheet 22 and backsheet 24 may be joined only at the longitudinal ends 28 as illustrated in FIG. 4 or, alternatively, may be intermittently joined across the transverse width of the sanitary napkin 20.

If desired, the joined transverse edge 32 may be formed by the opposed forces of the body and undergarment against the sanitary napkin 20. This embodiment is more effectively utilized with a relatively tightly fitting undergarment. Such an embodiment (not shown) resembles an open tube and has no transverse edge 32 where the topsheet 22 and backsheet 24 are adhesively joined, or joined by other means, as illustrated in the embodiments of FIGS. 2 and 4.

If such an embodiment is selected, it should have lesser Z-direction separation than the embodiments described above, otherwise excessive lateral shifting of one component of the sanitary napkin 20 relative to another component may occur. This lesser separation may be accomplished, for example, by providing longitudinally oriented pleats 52 having a lesser transverse depth. A longitudinally oriented pleat 52 having transverse depth of about 3 millimeters is suitable for this embodiment.

A sanitary napkin 20 according to the present invention may further comprise a transverse pleat (not shown), linking the topsheet 22 and the backsheet 24 at the unattached transverse edge 34. The transverse pleat is preferably made of a liquid impervious panel having one end joined to the inwardly oriented face of the topsheet 22 and one end joined to the inwardly oriented face 50 of the backsheet 24. If desired, the longitudinal edges of the transverse pleat may be joined to the means for controlling the separation of the topsheet 22 and backsheet 24. The transverse pleat provides the advantage that menses which may exceed the absorbent capacity of the core 26 or otherwise longitudinally migrate from or beyond the unattached transverse edge 34 of the napkin will be retained in the sanitary napkin 20.

In a less elegant embodiment (not shown), the means for controlling the separation of the topsheet 22 from the backsheet 24 of the sanitary napkin 20 may simply comprise flaccid material joining the topsheet 22 to the backsheet 24. As used herein, "flaccid material" refers to material intended to be slack in the Z-direction while the sanitary napkin 20 is not in the open position and allows for movement of such material and associated components in the Z-direction.

In such an embodiment, an excess of material of one of the backsheet 24 or topsheet 22 is joined to the other. Separation in the Z-direction may occur until the topsheet 22 and the backsheet 24 are restrained from further separating by the flaccid material becoming taut.

Such an embodiment is similar to those described above, except the means for controlling the separation of the topsheet 22 and backsheet 24 assumes random, undefined forms, which are not predetermined, when the sanitary napkin 20 is in the closed position. This is in contrast to the aforementioned embodiments where the means for controlling the separation of the topsheet 22 from the backsheet 24 have precise, repeatable and predetermined geometries for both the closed and opened positions.

What is claimed is:

1. A sanitary napkin having two spaced apart transverse edges, said sanitary napkin comprising:

a liquid pervious topsheet;

a liquid resistant backsheet joined to said topsheet along one said transverse edge and unattached to said topsheet along the other said transverse edge, whereby said backsheet may be separated from said topsheet at said unattached transverse edge;

an absorbent core associated with said topsheet and intermediate said topsheet and said backsheet; and a means for controlling the separation of said topsheet from said backsheet.

2. A sanitary napkin having two longitudinal ends and two spaced apart transverse edges, said sanitary napkin comprising:

a liquid pervious topsheet;

a liquid resistant backsheet, said topsheet and said backsheet being joined at one said transverse edge and unattached at the other said transverse edge, whereby said backsheet may be separated from said topsheet at said unattached transverse edge;

an absorbent core associated with said topsheet and intermediate said topsheet and said backsheet; and a longitudinally oriented pleat which joins said topsheet and said backsheet, whereby said longitudinally oriented pleat controls the separation of said backsheet from said topsheet.

3. A sanitary napkin having two transverse edges, said sanitary napkin comprising:

a liquid pervious topsheet;

a liquid resistant backsheet joined to said topsheet along one said transverse edge and unattached to said topsheet at the other said transverse edge, said backsheet being joined to said topsheet by flaccid material, whereby said topsheet may be separated from said backsheet at said unattached transverse edge until restrained by said flaccid material becoming taut; and an absorbent core associated with said topsheet and intermediate said topsheet and said backsheet.

4. A sanitary napkin according to claims 1, 2 or 3 wherein said core has two opposed faces, one face oriented towards the backsheet and one face oriented towards the topsheet, said backsheet has a face oriented towards said core and wherein said unattached transverse edge of said face of said core oriented towards said backsheet may be separated from said face of said backsheet oriented towards said core about 1 centimeter to about 6 centimeters.

5. A sanitary napkin according to claims 1, 2 or 3 wherein said core has two opposed faces, one face oriented towards said backsheet and one face oriented towards said topsheet, said backsheet has a face oriented towards said core and wherein said sanitary napkin forms an included angle between said face of said core oriented towards said backsheet and said face of said backsheet oriented towards said core of about 3° to about 60° when said core is separated from said backsheet at said unattached transverse edge.

6. A sanitary napkin according to claims 1, 2 or 3 further comprising a transverse pleat linking said topsheet and said backsheet at said unattached transverse edge.

7. A sanitary napkin according to claims 1, 2 or 3 further comprising a second unattached transverse edge.

8. A sanitary napkin according to claim 7, wherein said sanitary napkin has a first transverse end and a second transverse end spaced from said first transverse end, said joined transverse edge being intermediate said transverse ends and one-third of the longitudinal distance from said first transverse end to said second transverse end.

9. A sanitary napkin according to claim 2 wherein said longitudinally oriented pleat has a fold defining a transverse depth ranging from about 2 millimeters to about 15 millimeters.

* * * * *

UNITED STATES PATENT AND TRADEMARK OFFICE
CERTIFICATE OF CORRECTION

PATENT NO. : 5,007,906
DATED : April 16, 1991
INVENTOR(S) : THOMAS W. OSBORN, III and DEBORAH C. SCHMITZ It is certified that error appears in the above-identified patent and that said Letters Patent is hereby corrected as shown below:

On the cover page of the patent under Attorney, Agent, or Firm "Frederick" should be --Fredrick--.

Column 9, line 43, "Joining" should be --joining--.

Column 10, line 1, "1524" (bold print) should be --1524-- (without bold print).

Column 9-10 (second occurence) delete "predetermined width, and . . . a quarter-inch tape." (reference to Pat. No. 5,008,765)

Signed and Sealed this

First Day of September, 1992

Attest:

DOUGLAS B. COMER

*Attesting Officer*  *Acting Commissioner of Patents and Trademarks*